United States Patent [19]

Iida et al.

[11] Patent Number: 4,935,150

[45] Date of Patent: Jun. 19, 1990

[54] METHOD FOR REMOVING A PYROGEN

[75] Inventors: Hiroshi Iida, Yokohama; Koji Shintani; Satoshi Hanzawa, both of Ebina; Kazuhide Yoshikawa, Yokohama, all of Japan

[73] Assignee: Tosoh Corporation, Shinnanyo, Japan

[21] Appl. No.: 420,532

[22] Filed: Oct. 12, 1989

[30] Foreign Application Priority Data

Oct. 13, 1988 [JP] Japan ................................ 63-255913

[51] Int. Cl.$^5$ .......................... B01D 17/00; C02F 1/58
[52] U.S. Cl. .................................... 210/723; 210/645; 210/764
[58] Field of Search ............... 210/638, 639, 644, 645, 210/668, 690–692, 694, 702, 723, 726, 737, 738, 764, 766

[56] References Cited

U.S. PATENT DOCUMENTS

| | | | |
|---|---|---|---|
| 4,282,104 | 8/1981 | Pacini et al. | 210/764 X |
| 4,381,239 | 4/1983 | Chibata et al. | 210/692 X |
| 4,488,969 | 12/1984 | Hou | 210/692 X |
| 4,681,870 | 7/1987 | Balint, Jr. et al. | 210/691 X |
| 4,724,079 | 2/1988 | Sale et al. | 210/638 |

*Primary Examiner*—Tom Wyse
*Attorney, Agent, or Firm*—Oblon, Spivak, McClelland, Maier & Neustadt

[57] ABSTRACT

A method for removing a pyrogen from a pyrogen-containing sample solution, which comprises adding a calcium salt to the sample solution and separating the resulting precipitates.

6 Claims, No Drawings

METHOD FOR REMOVING A PYROGEN

The present invention relates to a method for removing a pyrogen from a pyrogen-containing sample solution.

When a drug or the like is administered directly into a body by e.g. intravenous injection, if the drug contains a pyrogen, pyrexia is likely to be induced. For a substance to be administered directly into a body, such as a drug, it is therefore important to prevent inclusion of a pyrogen. Various methods have been proposed not only to prevent inclusion of a pyrogen but also to remove it during the process for the preparation of a substance to be administered into a body.

Heretofore, the following methods have been known for the removal of a pyrogen from a pyrogen-containing sample solution (i.e. a solution containing a desired substance and a pyrogen):

(1) A method wherein the sample solution is subjected to gel filtration to remove the pyrogen (Japanese Unexamined Patent Publication No. 66885/1974)

(2) A method wherein the sample solution is treated with a resin to which a substance having affinity to substances other than the pyrogen, is fixed, to wash off the pyrogen (Japanese Unexamined Patent Publication No. 123869/1975)

(3) A method wherein the sample solution is treated with active carbon or a resin having histidine bonded thereto, to adsorb the pyrogen thereon (4) A method wherein the sample solution is treated with an ultrafilter to separate the pyrogen in a micelle state.

However, these conventional methods have a problem such that the removal of the pyrogen can not adequately be conducted depending upon the nature of the desired substance. Especially when the desired substance is highly hydrophobic or cationic, adsorption due to a hydrophobic or ionic interaction with the pyrogen is created, whereby the two substances can hardly be separated.

Further, for the removal of the pyrogen, it is necessary to select the method for the removal depending upon the nature of the desired substance. Therefore, various equipments for the respective methods are required. Furthermore, the conditions for the removal are required to be varied depending upon various conditions such as the concentration or the state of the desired substance. Therefore, the process and the operation for the removal tend to be cumbersome, and yet the removal rate of the pyrogen tends to be unstable.

In view of such various problems involved in the conventional methods, the present inventors have conducted extensive researches for a method of removing a pyrogen with a simple operation to attain a constant removal effect, which is applicable to solutions containing desired substances of various natures. As a result, they have found it possible to solve such problems by adding a calcium salt to the sample solution, and the present invention has been accomplished on the basis of this discovery.

The present invention provides a method for removing a pyrogen from a pyrogen-containing sample solution, which comprises adding a calcium salt to the sample solution and separating the resulting precipitates. In the method of the present invention, it is preferred to subject the sample solution to desalting prior to the addition of the calcium salt. In a preferred embodiment, the present invention provides a method for removing a pyrogen such as lipid A derived from *Escherichia coli* or its derivatives. Particularly, it provides a method for removing a pyrogen from a fractured bacterial cell solution containing proteins or polypeptides produced by recombinant bacteria.

Now, the present invention will be described in detail with reference to the preferred embodiments.

As described above, the sample solution is meant for a solution containing a desired substance and a pyrogen. For example, it may be a solution obtained by fracturing *Escherichia coli* having useful proteins produced therein, or a solution containing a pyrogen derived from *Escherichia coli*, which is obtained by subjecting the above-mentioned solution to a usual purification treatment such as centrifugal separation, membrane separation, filtration or ion exchange chromatography. Further, it may be a solution derived from e.g. Salmonella. Here, the desired substance includes polysaccharides in addition to naturally occuring proteins or proteins produced by genetic engineering.

In the present invention, the calcium salt to be added to the sample solution may be of an inorganic or organic type including, for example, calcium chloride, calcium carbonate, calcium acetate, calcium lactate, or calcium glycerophosphate.

A calcium salt is known to have blood coagulation effects. Therefore, it is necessary to separate the calcium salt at the final purification process of the desired substance. Accordingly, it is advisable to use it in a concentration as low as possible which is sufficient to precipitate the pyrogen. Such a low concentration may be determined by conducting a preliminary experiment. According to the test results of the present invention, good results are obtainable by adding the calcium salt to bring its concentration to a level of from 0.005 to 0.5 M.

By the addition of the calcium salt, the pyrogen precipitates. The precipitates of the pyrogen are then removed by a usual method such as centrifugal separation or filtration. Here, in order to complete the removal of the pyrogen in the solution, it is advisable to leave the sample solution after the addition of the calcium salt to stand still for a few hours. The time for leaving it to stand still may be determined taking into considerations the nature of the sample, the expected amount of the pyrogen and the deactivation of the desired substance during the operation and by conducting a preliminary experiment.

In the present invention, it is preferred that prior to the addition of the calcium salt to the sample solution, the sample solution is subjected to desalting to effectively induce the interaction of the calcium salt and the pyrogen. This operation is preferably conducted by dialysis since the operation is simple and the desalting effects are high.

According to the method of the present invention, it is possible to remove a pyrogen derived from *Escherichia coli*. Therefore, the present invention is useful for purifying a desired protein having useful physiological activities (including peptide) which is produced by genetic engineering in recent years. The method may be applied to a fractured bacterial cell suspension obtained by fracturing bacterial cells by a physical method or may be applied to the final purification stage of the desired protein. The specific method is as described above.

According to the present invention, a pyrogen can be removed by a simple operation. The present invention is a method comprising a very simple operation of adding a calcium salt to a sample solution, followed by separation of the resulting precipitates. Therefore, the method can be completed in a short period of time and can be applied to a large amount of the sample solution.

As is different from various conventional removal methods by chromatography, the present invention can be operated by an installation Of a simple construction.

Further, the present invention can be applied to various desired substances irrespective of whether the desired substance is e.g. hydrophobic or cationic.

Now, the present invention will be described in detail with reference to Examples. However, it should be understood that the present invention is by no means restricted by such specific Examples.

EXAMPLE 1

5 mg of porcine plasmin (PLASMIN No. 98644, manufactured by SIGMA Co.) and 11 mg of bovine hemoglobin (Hemoglobin from Bovine 082-00122, manufactured by Wako Junyaku Kogyo K.K.) were, respectively, dissolved in 5 ml of water containing no pyrogen to obtain two solutions for each sample (a sample solution and a control solution for each sample). Each solution was dialyzed against water containing no pyrogen.

After the dialysis, to 600 μl of each sample solution, the same amount of a 10 mM calcium chloride solution was added, and the mixture was left to stand still overnight. To the control solution, water containing no pyrogen was added in an amount of 600 μl instead of the 10 mM calcium chloride solution, and the mixture was left to stand still overnight.

Four types of solutions were centrifugally separated at 15,000×g for 30 minutes to obtain the respective supernatants.

With respect to the four solutions, the amounts of the pyrogens were measured by Toxicolor System (tradename, manufactured by Seikagaku Kogyo K.K.). The protein concentrations with respect to the four solutions were measured by using BCA Protein Assay Reagent (tradename, manufactured by Pierce Chemical Co.) by using bovine serum albumin (ALBUMIN No. A-7906, manufactured by SIGMA Co.) as the standard protein. The results of the measurements are shown in Table 1. In Table 1, symbol +indicates the sample to which- the calcium chloride solution was added, and symbol - indicates the sample to which water containing no pyrogen was added instead of the calcium chloride solution. The protein concentration is indicated based on the concentration of the sample to which water was added, being 100%.

EXAMPLE 2

Human prourokinase (hereinafer referred to as prourokinase) was prepared by culturing K12 strain of Escherichia coli transformed with a plasmid having a gene coded with prourokinase (this plasmid was obtained from Escherichia coli deposited under deposition No. 8341 at Fermentation Research Institute, Agency of Industrial Science and Technology, Ministry of International Trade and Industry). After the cultivation, 100 g of the bacteria cells were suspended in 1 l of a 0.1 M tris-HCl(Tris: tris(hydroxymethyl) aminomethane) buffer solution (pH 8.0) and then fractured by means of Gorin homogenizer (manufactured by Manton Gorin Co.). The fractured cell solution was subjected to centrifugal separation to obtain an insoluble fraction.

The insoluble fraction was suspended in 1 l of a 0.1 M Tris-HCl (Tris: tris(hydroxymethyl)aminomethane) buffer solution (pH 8.0), and 1 l of a 8 M guanidine hydrochloride solution was added thereto. The mixture was treated for solubilization for 2 hours. Then, 14 l of a 50 mM Tris-HCl buffer solution (pH 8.0) containing 0.2 mM reduced glutathione, 0.02 mM oxidized glutathione and 0.6 M guanidine hydrochloride, was added for dilution, and the mixture was left to stand at 25° C. for 16 hours for renaturation (or folding).

After the renaturation (or folding), 1,800 g of ammonium sulfate was added to the solution (16 l), and the mixture was left to stand at 4° C. overnight and then subjected to centrifugal separation. The supernatant was treated with an ion exchange resin (SP-Toyopearl 650-S, tradename, manufactured by TOSOH CORPORATION) to obtain a prourokinase fraction. This fraction was used as a sample solution. The prourokinase activity of this sample solution was 1,050,000 units.

The sample solution was dialyzed overnight against water containing no pyrogen. Then, to 10 ml of the sample solution, 0.7 g of calcium chloride dihydride was added, and the mixture was left to stand still for one hour. Then, the precipitates were removed by filtration.

The prourokinase activity of the prourokinase solution thus obtained was 980,000 units. Thus, 93% of the activity was maintained.

The content of the pyrogen decreased to 0.14 ng per 10,000 units of the prourokinase while it was 8.9 ng per 10,000 units of the prourokinase prior to the addition of calcium chloride.

The measurement of the amount of the pyrogen was conducted in the same manner as in Example 1. The measurement of the activity of the prourokinase was conducted by adding plasmin to the solution to convert the prourokinase to urokinase, whereupon the decomposition activity of the urokinase against synthetic substrate S-2444 (manufactured by Kavivitrum AB, Sweden) was measured (see Khono et al., Biotechnology 2,628, 1984).

TABLE 1

|  |  | Protein concentration (%) | Amount of pyrogen per Amount of protein (ng/mg) |
|---|---|---|---|
| Plasmin | − | 100 | 2.4 |
|  | + | 91 | 0.76 |
| Hemoglobin | − | 100 | 75 |
|  | + | 100 | 36 |

What is claimed is:

1. A method for removing a pyrogen from a pyrogen-containing sample solution, which comprises adding a calcium salt to the sample solution and separating the resulting precipitates.

2. The method according to claim 1, wherein the sample solution is subjected to desalting prior to the addition of the calcium salt.

3. The method according to claim 1, wherein the pyrogen is lipid A derived from Escherichia coli or its derivatives.

4. The method according to claim 1, wherein the sample solution is a solution containing a protein or a polypeptide produced by recombinant Escherichia coli.

5. The method according to claim 1, wherein the sample solution is a solution containing a protein or a polypeptide contaminated by the pyrogen.

6. The method according to claim 5, wherein the pyrogen is lipid A.

* * * * *